US011567189B2

(12) United States Patent
Aflatouni et al.

(10) Patent No.: US 11,567,189 B2
(45) Date of Patent: Jan. 31, 2023

(54) OPTICALLY ASSISTED ULTRA-WIDEBAND (UWB) IMAGER

(71) Applicant: THE TRUSTEES OF THE UNIVERSITY OF PENNSYLVANIA, Philadelphia, PA (US)

(72) Inventors: Firooz Aflatouni, Penn Valley, PA (US); Farshid Ashtiani, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 49 days.

(21) Appl. No.: 16/969,998

(22) PCT Filed: Feb. 15, 2019

(86) PCT No.: PCT/US2019/018261
§ 371 (c)(1),
(2) Date: Aug. 14, 2020

(87) PCT Pub. No.: WO2019/161234
PCT Pub. Date: Aug. 22, 2019

(65) Prior Publication Data
US 2021/0103047 A1 Apr. 8, 2021

Related U.S. Application Data

(60) Provisional application No. 62/631,175, filed on Feb. 15, 2018.

(51) Int. Cl.
*G01S 13/89* (2006.01)
*G01S 7/03* (2006.01)
(Continued)

(52) U.S. Cl.
CPC ............. *G01S 13/89* (2013.01); *G01S 7/03* (2013.01); *G01S 13/0209* (2013.01); *H04N 5/30* (2013.01); *H01Q 21/00* (2013.01)

(58) Field of Classification Search
CPC ........ G01S 13/89; G01S 7/03; G01S 13/0209; H04N 5/30; H01Q 21/00
See application file for complete search history.

(56) References Cited

U.S. PATENT DOCUMENTS 5,573,012 A   11/1996   McEwan
6,417,957 B1   7/2002   Yao
(Continued)

OTHER PUBLICATIONS

Brovoll et al., "Time-Lapse Imaging of Human Heart Motion With Switched Array UWB Radar", in IEEE Transactions on Biomedical Circuits and Systems, Oct. 2014, vol. 8, No. 5, pp. 704-715.
(Continued)

*Primary Examiner* — Jae N Noh
(74) *Attorney, Agent, or Firm* — BakerHostetler

(57) ABSTRACT

Provided are systems and methods of using of optical delay lines in RF imagers, e.g., Ultra-wideband (UWB) imagers. In an embodiment, a modulator can be configured to convert radio-frequency signals to optical signal. First and second optical delay lines delay respective first and second optical signals converted by the modulator, and a photodetector can convert the delayed optical signals to at least one electrical signal corresponding to at least one pixel of a radio frequency image. The disclosed systems and methods can also further form a radio-frequency image based on output from the photodetector. In still further embodiments, the photodetector can receive modulated optical signals from an array of optical delays. Also provided are related methods of using the disclosed systems and devices.

19 Claims, 8 Drawing Sheets

(51) Int. Cl.
  H04N 5/30    (2006.01)
  H01Q 21/00   (2006.01)
  G01S 13/02   (2006.01)

(56) References Cited

U.S. PATENT DOCUMENTS

| | | | |
|---|---|---|---|
| 2008/0252524 A1* | 10/2008 | Chu | H01Q 3/2682 |
| | | | 342/375 |
| 2009/0115650 A1* | 5/2009 | Tietjen | H04B 1/0007 |
| | | | 341/155 |
| 2011/0150485 A1 | 6/2011 | Seidel et al. | |
| 2013/0169483 A1 | 7/2013 | Vidal et al. | |
| 2014/0192161 A1 | 7/2014 | Murakowski et al. | |
| 2017/0041068 A1 | 2/2017 | Murakowski et al. | |
| 2017/0063460 A1 | 3/2017 | Hajimiri et al. | |
| 2017/0085323 A1 | 3/2017 | Schuetz et al. | |

OTHER PUBLICATIONS

Catherwood et al., "Internet of Things-Enabled Hospital Wards: Ultrawideband Doctor-Patient Radio Channels", in IEEE Antennas and Propagation Magazine, Jun. 2018, vol. 60, No. 3., pp. 10-18.

Chavez-Santiago et al., "Ultrawideband Signals in Medicine (Life Sciences)", in IEEE Signal Processing Magazine, Nov. 2014, vol. 31, No. 6, pp. 130-136.

Chu et al.,"A CMOS UWB camera with 77 simultaneous active pixels", IEEE International Solid-State Circuits Conference, Feb. 2008, pp. 120-121.

Chu et al., "An Integrated Ultra-Wideband Timed Array Received in 0.13 m CMOS Using a Path-Sharing True Time Delay Architecture", in IEEE Journal of Solid-State Circuits, Dec. 2007, vol. 42, No. 12, pp. 2834-2850.

Chu et al., "True-Time-Delay-Based Multi-Beam Arrays", in IEEE Transactions on Microwave Theory and Techniques, Aug. 2013, vol. 61, No. 8, pp. 3072-3082.

Elbahhar et al., "Using UWB Gaussian pulses for inter-vehicle communications", in IEEE Proceedings—Communications, Apr. 2005, vol. 152, No. 2, pp. 229-234.

Hashemi et al., "Integrated true-time-delay-based ultra-wideband array processing", in IEEE Communications Magazine, Sep. 2008, vol. 46, No. 9, pp. 162-172.

Immoreev et al., "UWB radar for patient monitoring" in IEEE Aerospace and Electronic Systems Magazine, Nov. 2008, vol. 23, No. 11, pp. 11-18.

Kidera et al., "High-Resolution in 3-D Imaging Algorithm With an Envelope of Modified Spheres for UWB Through-the-Wall-Radars", in IEEE Transactions on Antennas and Propagation, Nov. 2009, vol. 57, No. 11, pp. 3520-3529.

Kikkawa et al., "Gaussian Monocycle Pulse Transmitter Using 0.18 m CMOS Technology With On-Chip Integrated Antennas for Inter-Chip UWB Communication", in IEEE Journal of Solid-State Circuits, May 2008, vol. 43, No. 5, 1303-1312.

Lee et al., "A Novel Non-Contact Heart Rate Monitor Using Impulse-Radio Ultra-Wideband (IR-UWB) Radar Technology", Scientific Reports 8, Article No. 13053, 2018.

Liang et al., "Ultra-Wideband Impulse Radar Through-Wall Detection of Vital Signs", Scientific Reports 8, Article No. 13367, 2018.

LifeWave Biomedical (on-line), at http://www.lifewavebiomed.com.

Ma et al., "Ultralow loss single layer submicron 5 silicon waveguide crossing for SOI optical interconnect", Optics Express, 2013, vol. 24, No. 21.

Mahfouz et al., "Investigation of High-Accuracy Indoor 3-D Positioning using UWB Technology", in IEEE Transactions on Microwave Theory and Techniques, Jun. 2008, vol. 56, No. 6, pp. 1316-1330.

Nagra et al., "Distributed analog phase shifters with low insertion loss", in IEEE Transactions on Microwave Theory and Techniques, Sep. 1999, vol. 47, No. 9, pp. 1705-1711.

Novack et al., "A 30 GHz silicon photonic platform", In Proc. SPIE 8781, Integrated Optics: Physics and Simulations, 2013.

Park et al., "A 15-40 GHz CMOS True-Time Delay Circuit for UWB Multi-Antenna Systems" in IEEE Microwave and Wireless Components Letters, Mar. 2013, vol. 23, No. 3, pp. 149-151.

Rahman et al., "Electromagnetic Performances Analysis of an Ultra-wideband and flexible Material Antenna in Microwave Breast Imaging: To Implement a Wearable Medical Bra", Scientific Reports 6, Article No. 38906, 2016.

Rodenbeck et al., "Ultra-wideband low-cost phased-array radars", in IEEE Transactions on Microwave Theory and Techniques, Dec. 2005, vol. 53, No. 12, pp. 3697-3703.

Roderick et al., "Silicon-Based Ultra-Wideband Beam-Forming", in IEEE Journal of Solid-State Circuits, Aug. 2006, vol. 41, No. 8, pp. 1726-1739.

Song et al., "Detectability of Breast Tumor by a Hand-held Impulse-Radar Detector: Performance Evaluation and Pilot Clinical Study", Scientific Reports 7, Article No. 16353, 2017.

Staderini, "UWB radars in medicine", IEEE Aerospace and Electronic Systems Magazine, 2002, vol. 17, Issue 1, pp. 13-18.

Tan et al., "A 79GHz UWB pulse-compression vehicular radar in 90nm CMOS", in Microwave Symposium Digest (MTT), Jun. 2012, vol. 1, No. 3, 17-22.

Xuan et al., "Silicon modulator for 40 GB/s NRZ-OOK metro networks in O-band", Opt. Express 22, 28284-28291, 2014.

Yang et al., "Ultra-wideband communications: an idea whose time has come", in IEEE Signal Processing Magazine, Nov. 2004, vol. 21, No. 6, pp. 26-54.

Yong et al., "An Overview of Ultra-Wideband Technique Application for Medical Engineering", IEEE/ICME International Conference on Complex Medical Engineering (CME), Beijing, May 2007.

Fakharzadeh, Mohammad et al., "Design and Analysis of Ultra-Miniaturized Meandering Photonic Crystals Delay Lines", IEEE Transactions on Advanced Packaging, May 2008, vol. 31, No. 2, pp. 311.

* cited by examiner

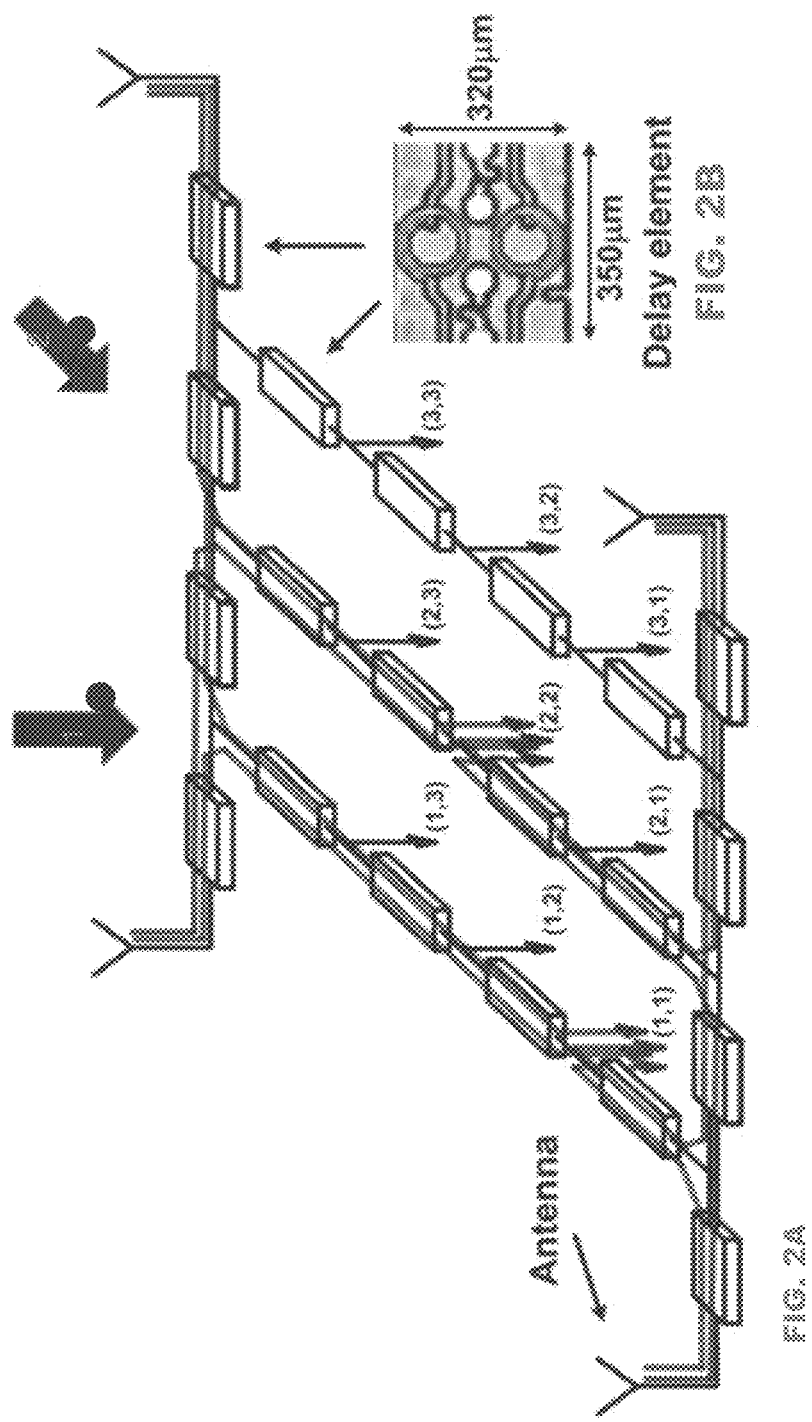

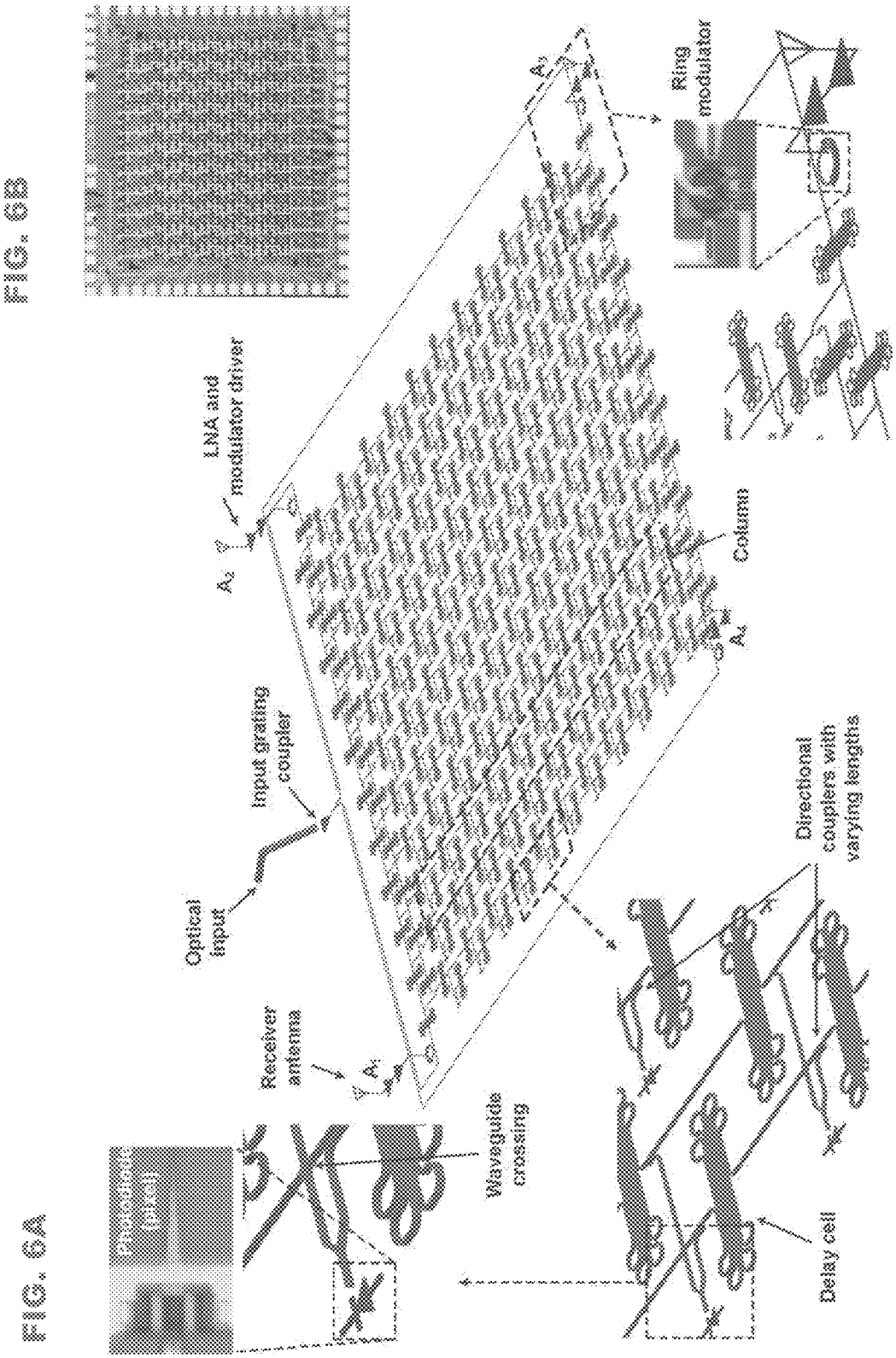

OPTICALLY ASSISTED ULTRA-WIDEBAND (UWB) IMAGER

CROSS-REFERENCE TO RELATED APPLICATIONS

This application is the National Stage Application of International Patent Application No. PCT/US2019/018261, filed Feb. 15, 2019, which claims priority to and the benefit of U.S. Patent Application No. 62/631,175 (filed Feb. 15, 2018), which foregoing applications are incorporated herein in their entireties for any and all purposes.

TECHNICAL FIELD

The present invention relates generally to the field of radiofrequency imaging devices, in particular to systems and methods for using optical delay lines in ultra-wideband imagers.

BACKGROUND

Ultra-wideband (UWB) RF/mm-wave/THz imaging systems can achieve high depth resolution and image through optically opaque objects, thereby enabling many applications ranging from tracking and positioning, surveillance, communication, localization, vehicular radar, imaging in various weather conditions, radar, and low power communication for internet-of-things (IoT). In medicine, UWB systems have been used, for example, for cancer cell detection, human vital sign monitoring, patient monitoring; and imaging of heart motions and respiration rate.

UWB imagers are conventionally implemented using either scanning antenna arrays or multi-beam antenna arrays. True-time delay (TTD) based implementations are commonly used to avoid signal distortion caused by narrowband phase shifters. However, large delay element size, high power consumption due to electrical loss, and electromagnetic interference susceptibility are all challenges in these system, thus limiting large scale implementations.

In addition, integrated UWB imagers with large number of on-chip pixels can form and steer a narrow beam enabling realization of high resolution, low power, low cost, and portable UWB imaging systems. The major challenges in integration of such imaging system on conventional electronic platforms (such as standard CMOS processes) are the realization of on-chip wide-band variable TTD lines with small steps and large overall delay as well as the delay-sum beam forming network.

The signals received by the antenna are passed through an electrical delay line. The area required for the electrical delay lines, however, makes the realization of an RF imager with large number of pixels impractical. Moreover, due to limited quality factor of inductors and capacitors at RF frequencies in standard CMOS processes, these electrical delay lines, e.g., LC (Lumped Constant) delay lines, introduce a large propagation loss. Accordingly, there is a need in the art for improved imaging systems.

SUMMARY

In meeting the described needs, the present disclosure provides a multi-beam communication system that exhibits resistance to the multi-path effect in receivers, offers higher signal-to-noise ratio (SNR), and is more compatible with multi-user environments than existing approaches.

This disclosure provides, inter alia, systems and methods of using of optical delay lines in RF/mm-wave/THz imagers. Optical delay lines can reduce the size and power consumption by many orders of magnitude compared to the use of electrical delay lines. Optical delay lines also generally have significantly lower loss and occupy smaller chip area than electrical delay lines, and can usually be realized using nano-waveguide propagation delay, resonator group delay, or group delay of cascaded optical resonators.

As described herein, the disclosed technology can comprise a nanophotonic integrated UWB imager wherein the TTD network is implemented in optical domain. Low-loss photonic TTD elements that are, e.g., 20 times smaller than their electrical counterparts at a significantly lower loss are provided. As but some examples, a delay resolution of 9.8 ps is achieved that corresponds to 5° spatial resolution for antenna spacing of 7 cm. The photonic chip is implemented on IME 180 nm SOI process and has an area of 4 mm$^2$.

In one embodiment, a modulator can be configured to convert radio-frequency signals to optical signal. A first optical delay line is configured to delay a first optical signal based on the output optical signal by the first modulator, and a second optical delay line is configured to delay a second optical signal based on the output optical signal by the first modulator. A photodetector can convert the delayed optical signals to at least one electrical signal corresponding to at least one pixel of a radio frequency image.

In another embodiment, an imagine module can be configured to determine a value for a pixel of the radiofrequency image based on the electrical signal. In other embodiments, one or more antennas electrically connected to a second modulator can be configured to receive the radiofrequency signal. Furthermore, the system can comprise a processor having at least memory comprising executable instructions to form a radiofrequency image based, in part, on the output of the photodetector.

Additionally, a system can comprise an antenna, a modulator receiving an electrical signal, an array of optical delays received optical signals from the modulator, and a photodetector that receives optical signals from the array of optical delays.

Also provided are related methods of using the disclosed systems and devices.

BRIEF DESCRIPTION OF THE DRAWINGS

Various non-limiting embodiments are further described with reference to the accompanying drawings in which:

FIG. 2(a) depicts a block diagram of the 2D multi-beam imager as an extension of the 1D structure FIG. 2(b) depicts an electrical delay line element.

FIG. 6 depicts a block diagram of an 11×11 photonic UWB imager.

DETAILED DESCRIPTION OF ILLUSTRATIVE EMBODIMENTS

Figure 1B:
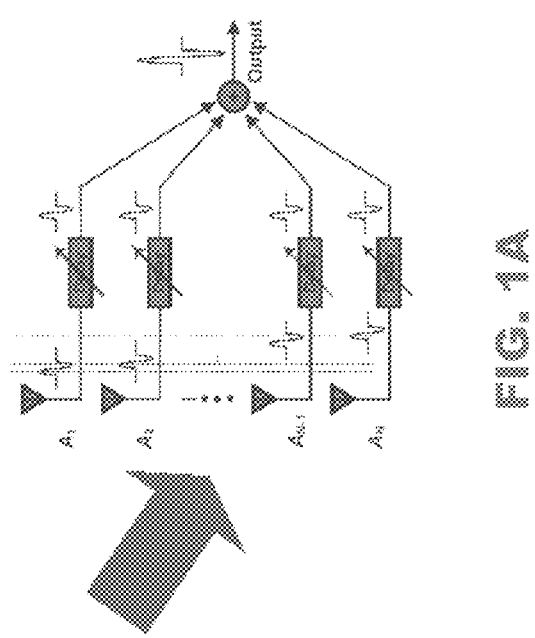
FIG. 1(b) depicts a block diagram of a multi-beam 1D array imager.

The present disclosure may be understood more readily by reference to the following detailed description taken in connection with the accompanying figures and examples, which form a part of this disclosure. The following section provides description of the non limiting figures attached hereto. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention.

The present disclosure relates to integrated photonic UWB imagers wherein the received radio frequency UWB signal can be up-converted to the optical domain using optical ring modulators. The optical signals can be delayed in a nanophotonic TTD cell network. In various embodiments disclosed herein, delayed optical signals are combined and photoetched using a matrix (e.g., 11×11) of photodiodes acting as the pixels of the imager. The photocurrents are further amplified and energy detected to form the corresponding image.

Compared to the state-of-the-art all electrical integrated RF UWB imagers on CMOS4, the implemented photonic assisted UWB imagers benefit from photonic delay lines with smaller area (e.g., 20× smaller) and significantly lower power consumption while providing the same delay. The photonic distribution, delay line implementation, and beamforming enable the scalability of the disclosed architecture to an imager with large number of pixels, a task for which no simple integrated all-electrical solution exists. Furthermore, unlike electronic implementations, the photonic delay lines are immune to undesired magnetic coupling and electromagnetic interference. In embodiments, the imager is capable of receiving, e.g., 121 simultaneous beams. As one example, the TTD cell delay amount can be 9.8 ps, and together with a 2×2 UWB antenna array with 7 cm antenna spacing, can result in a spatial resolution of 5° and coverage range of ±25°.

Figures

In UWB imagers, a narrow time domain pulse (spread out over a wide frequency range in RF or mm-wave regime), often a monocycle, is used to illuminate the target object and the reflected pulse is received using a wideband antenna array. FIG. 1(a) provides an exemplary architecture of a single-beam one-dimension (1-D) UWB receiver antenna array, in which N antennas receive the reflected pulse at different times depending on the angle of incidence of the incoming pulse. The received pulses can be aligned using variable true time delay (TTD) elements placed in each path and constructively power combined at the output. In this case, each delay setting corresponds to steering the antenna array to a certain spatial angle of incidence. Therefore, an image can be formed by dynamically changing the TTD settings to scan a range of angles. In contrast, a multi-beam antenna array is capable of spanning a range of spatial angles simultaneously and receive signal from different directions at the same time, which is useful in imaging applications.

Conventionally, the on-chip delay lines are implemented either by setting the length of a transmission line or through changing the wave propagation velocity in a waveguide or a transmission line. Given the wave velocity in a typical on-chip transmission line and the large propagation loss resulting from the loss in the silicon substrate in standard CMOS processes, the length of the transmission line required to realize the maximum delay required in practical UWB imagers and the associated propagation loss is too large to be implemented on-chip. An alternative approach is to implement the delay element using a transmission line periodically loaded with series inductors and shunt capacitors (LC segments) to increase the propagation constant and effectively increasing the delay per length of the line. In this case, while for a given delay, the length of the transmission line is reduced compared to the un-loaded transmission line, the delay line LC segments occupy a large area due to large size of on-chip inductors. Furthermore, due to the limited quality factor of inductors and capacitors caused by the silicon substrate loss, each LC segment of the line introduces a considerable amount of propagation loss that often is compensated using repeating amplifiers. The resulting large area and high power consumption of the on-chip delay lines as well as sensitivity to magnetic coupling and venerability to electromagnetic interference can limit the scalability of on-chip UWB imagers implemented on standard electronic processes. A novel 7×7-pixel UWB imager based on delay sharing architecture is introduced which significantly reduces the number of delay elements for the same imaging performance. In embodiments, the large on-chip delay element has an area of 300 μm by 200 μm and the chip power consumption is about 1 W.

High optical confinement and low propagation loss offered by nanophotonic waveguides together with a large bandwidth available around the optical carrier make the CMOS compatible silicon photonics platforms good candidates for photonic assisted electrical signal processing including implementation of UWB delay lines and delay-sum beam-formers. Furthermore, large group index in nanophotonic SOI waveguides, corresponding to lower wave propagation velocity compared to electrical transmission lines, results in larger delay per length compared to electrical delay lines which together with high degree of confinement and significantly lower propagation loss make the optical delay lines far more compact than the electrical delay lines for the same delay and with significantly lower propagation loss.

Figure 1A:
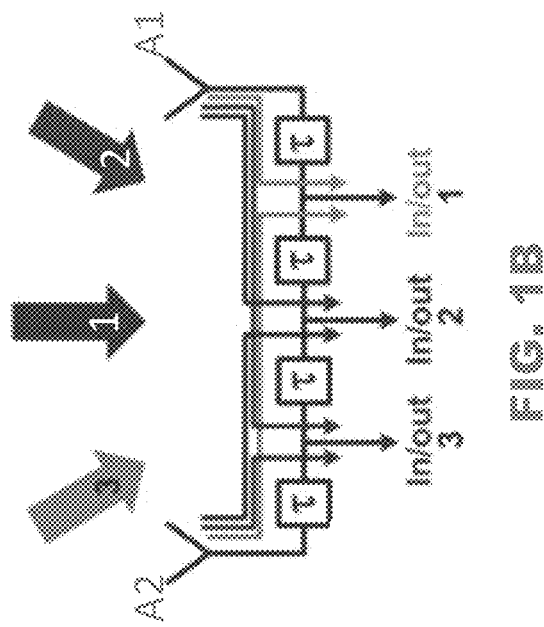
FIG. 1(a) depicts a block diagram of a 1D, single beam antenna array.

FIG. 1(b) provides an example architecture of a multi-beam 1D array imager where fixed TTD elements in a delay-sharing architecture are used. Two antennas are connected to the ends of a 1D delay line. Depending on the incident angle, two antennas receive the signal with different delays. As a result, the received signals undergo different delays on chip to coherently add at a certain output.

If an electromagnetic wave is received by the two antennas at the same time (i.e., normal incidence), the signal (labeled as beam 1) is detected at the middle point of this delay line at tap point 2. Thus, the two signals are combined coherently after each passes through the same amount of delay of 2τ. For the case that the pulse impinges on the array from beam 2, assuming that the unit delay element has the delay of τ, the signal that reaches the left antenna 2τ after being received by the right antenna will be constructively combined with the signal detected by the right antenna at the tap point 3. Similarly, beam 3 illustrates that a signal reaching the right antenna 2τ after being received by the left antenna will. be constructively combined with the signal detected by the left antenna at tap point 1. The delay sharing architecture in FIG. 1(*b*) can be extended into a 2D antenna array as shown in FIG. 2(*a*).

FIG. 2(*a*) shows a block diagram of an exemplary 2D multi-beam imager as an extension of the 1D structure. For example, for the case of normal incidence, when the signal reaches all 4 antennas at the same time (labeled as beam 1), the signal is detected at pixel (2, 2) in the middle of the pixel array. Similarly, beam 2, pointing to the center of the array from top right corner, is detected at tap (1, 1) as pictorially illustrated. Using similar architecture, a 7×7 pixel array can be formed (see, e.g., T. Chu and H. Hashemi) where each electrically realized LC delay line element (providing 8 ps time delay) occupies 350×320 $\mu m^2$ area.

This architecture can be realized using smaller number of delay elements per pixel compared to other prior methods, (see, e.g., T. Chu and H. Hashemi), However, the area required for the electrical delay lines makes realization of RF imager with large number of pixels impractical. Moreover, due to limited quality factor of inductors and capacitors at RF frequencies in standard CMOS processes, these LC delay lines introduce a large propagation loss.

To overcome this loss, active amplitude equalization is often employed, which results in more power consumption and chip area. Compared to electrical delay lines, optical delay lines have generally significantly lower loss and occupy smaller chip area and can usually be realized using nano-waveguide propagation delay, resonator group delay, or group delay of cascaded optical resonators. To use optical delay lines in electrical systems, the electrical signal is suitably up-converted to the optical domain, optically delayed, and down-converted back to electrical domain.

Besides low-loss optical delay lines, different types of resonators, ring modulators and photodiodes with mm-wave range bandwidth available in silicon-on-insulator platforms play a key role in realization of the optically enabled mm-wave delay lines. These optical delay lines can also be implemented in other platforms and processes (such as InP, GaAs, etc.) and using different optical structures such as (waveguides, ring and disk resonators, grating structures, coupled resonators, etc.).

Figure 3:
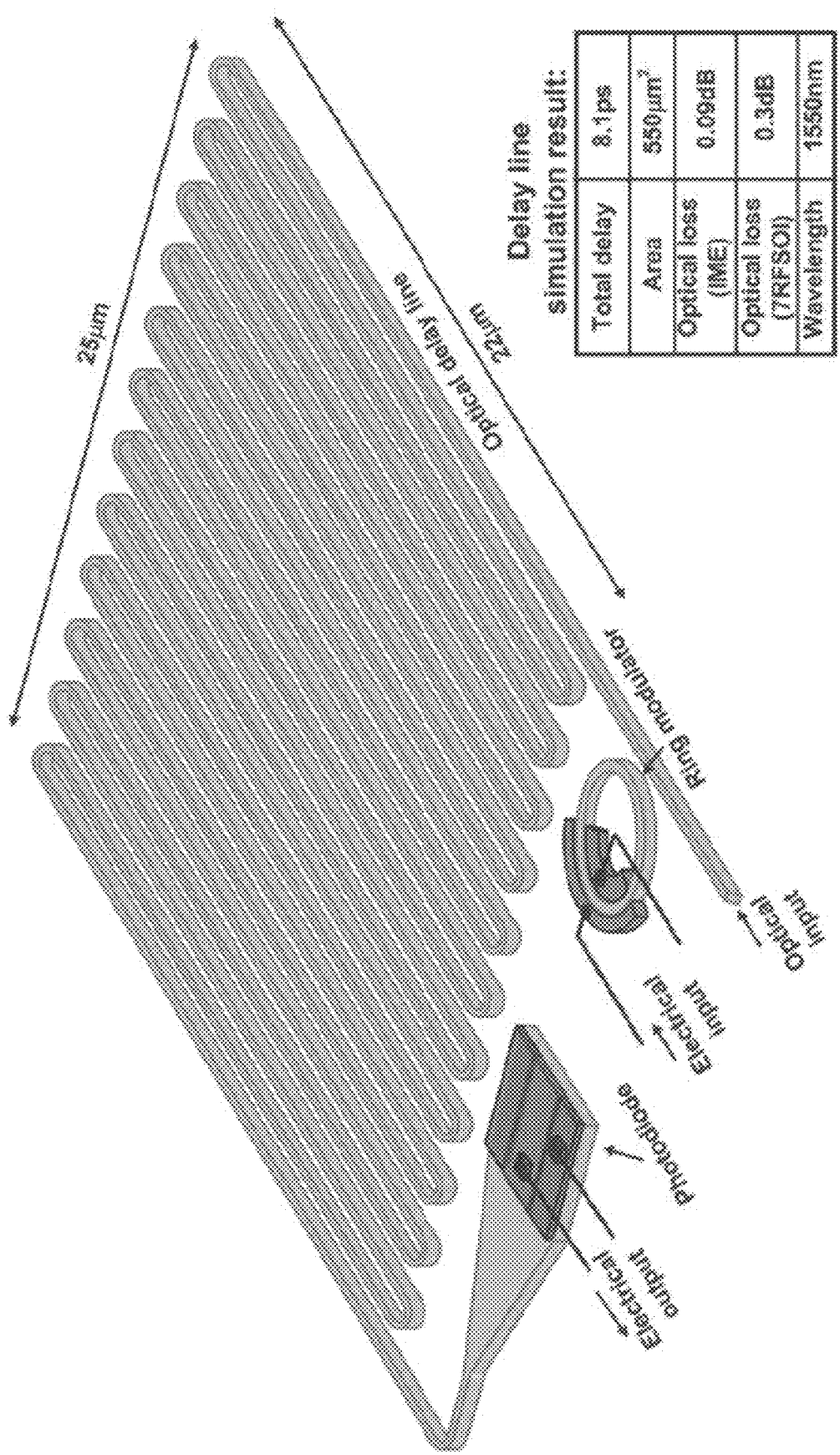
FIG. 3 depicts an embodiment of a single element optically-assisted electrical delay line.

One embodiment of a single element optically-assisted electrical delay line is shown in FIG. 3. First, the input RF signal in the form of:

$$V_{RF}(t) = \alpha_0 \cos(\omega_{RF} t) \quad [1]$$

is used to intensity modulate a laser output using a ring modulator.

Assuming the laser output electric field of $E_L = \sqrt{P_0} e^{j\omega_0 t}$, the ring modulator output can be approximated as:

$$E_M \approx \sqrt{P_0} e^{j(\omega_0 t + (\pi/V_\pi) V_{RF}(t))} \quad [2]$$

where $\alpha_0$, $\omega_{RF}$, $P_0$, $\omega_0$, and $V_\pi$ are the amplitude of the RF signal, RF signal frequency, laser intensity, laser frequency, and the modulator gain, respectively.

The modulator output is delayed using an optical delay line. The delayed optical signal is written as:

$$E_d \approx \beta \sqrt{P_0} e^{j(\omega_0(t-\tau) + (\pi/V_\pi) V_{RF}(t-\tau))} \quad [3]$$

where $\beta$ and $\tau$ represent the optical loss and the propagation delay of the delay line, respectively.

The fundamental component of the electrical current after photodetection is proportional to $P_0 J_1((\alpha_0/V_\pi)\pi)\cos(\omega RF(t-\tau))$ which indicates the electrical signal is delayed by the amount of optical propagation delay. The delay line is a meandered waveguide that produces 8.1 ps delay while occupying a 550 $\mu^2$ area. Compared to an all-electrical delay line (see, e.g., T. Chu and H. Hashemi; FIG. 2(*a*)), this optical delay line is 200 times smaller while providing the same delay at much smaller propagation loss.

The optical delay line in FIG. 2(*b*) is designed in IME standard SOI photonic process and IBM7RF-SOI standard CMOS process where simulations show propagation loss of 0.09 dB and 0.3 dB, respectively. Other types of optical delay lines and equivalent delay (such as resonators, grating waveguides, and similar structures) implemented on various platforms can be used to implement the disclosed technology.

FIG. 3 depicts one embodiment of the disclosed optically assisted multi-beam RF/mmwave/THz imager, where RF signals are delayed optically. Although a 4×4 pixel RF imager is shown for simplicity, this architecture can be scaled to large number of pixels and can be implemented using other optical structures such as resonators and grating waveguides, coupled structures (and similar) and on various platforms and processes such as SOI, InP, GaAs and similar. Four UWB patch antennas are placed at the corners of the imager and are used to detect the impinging RF signals. The detected signals are amplified using low noise amplifiers (LNA).

The output of each LNA is used to drive a ring modulator using a modulator driver. In one embodiment, a laser, e.g., emitting in 1550 nm band, is coupled into the imager chip using a grating coupler. The coupled light is split into 4 branches and is guided to the input of each ring modulator where they are modulated by the detected impinging RF signal. Five identical 1D delay line arrays are used for simultaneous multi-beam detection. For simplicity, only the components inside the top 1D delay line array are depicted.

To avoid undesired interference between counter propagating optical waves launched from the two ends of the 1D delay line array, two separate sets of series delay elements can be used. The top set processes the signal detected by the antenna on left propagating from left to right and the bottom set processes the signal propagating from right to left. Each delay element is identical to the one depicted in FIG. 3 (8.1 ps).

Figures 4A, 4B:
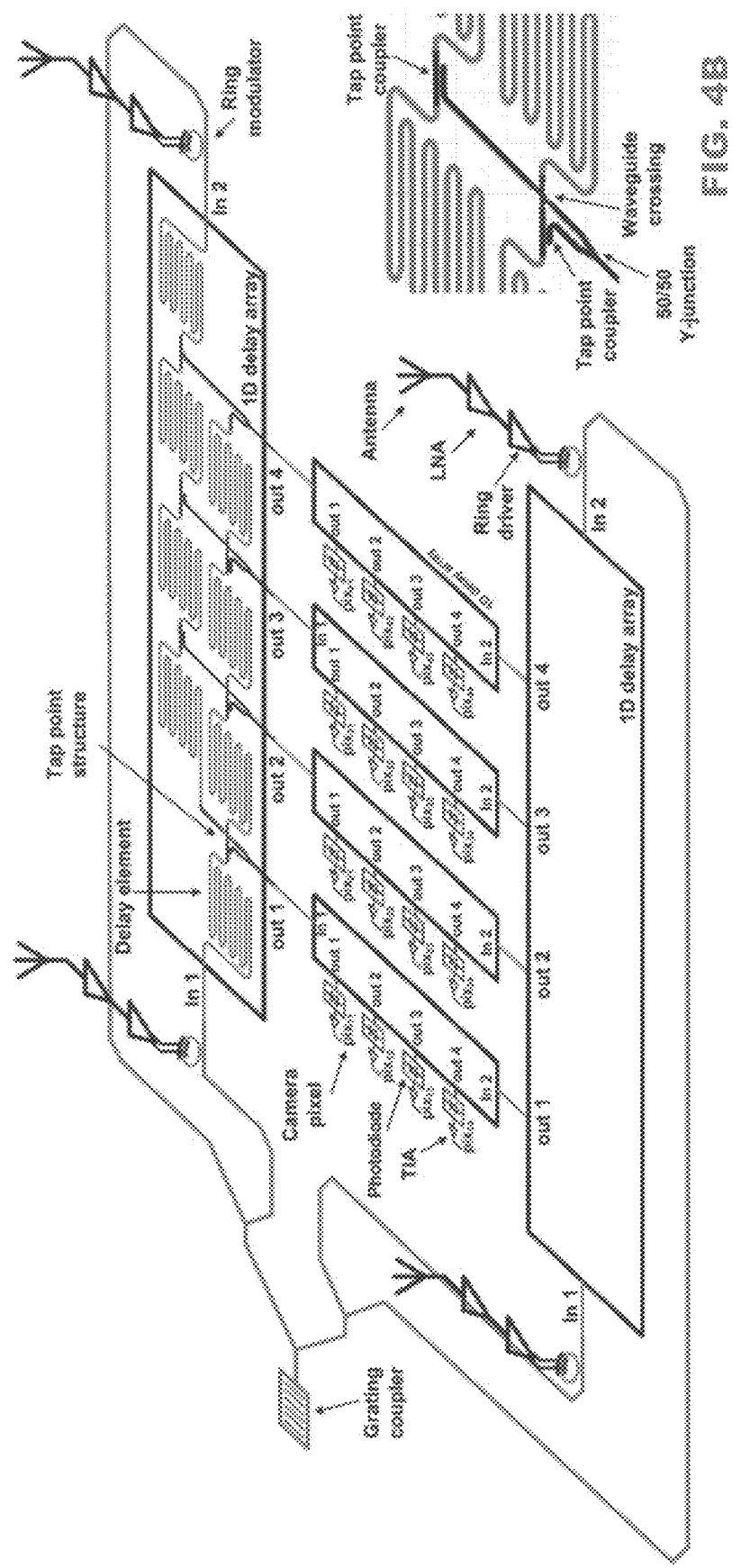
FIG. 4(a) depicts block diagram of the 2D multi-beam imager.
FIG. 4(b) depicts an embodiment of the tap point structure

Tap points of the top set is/are combined with its corresponding tap point of the bottom set to mimic the functionality of the bi-directional electrical delay line presented in FIG. 1. The tap point structure is shown in FIG. 4(*b*). In each tap point, a 50/50 Y-junction is used to combine 1/N of the total power in the top set of delay element (sampled using the tap coupler) with 1/N of the total power of the bottom set (sampled using another tap coupler).

A waveguide crossing with typical loss less than 0.1 dB and isolation better than 40 dB is used to route the light from the top tap coupler to the Y-junction as there is usually only one dedicated layer available for optical waveguide realization. The $i^{th}$ tap coupler has the coupling ratio of $(1/(N+1-i))/((N-i)/(N+1-i))$ as the power of the signals entering each 1D delay line array must be the same and equal to 1/N of the total power (N is the number of the tap points which is 4 in FIG. 4(*a*)).

The output of the vertical 1D delay line arrays are connected to the active pixels. Each active pixel consists of a photodetector and a trans-impedance amplifier (TIA). The output voltage of the TIAs are converted to digital and processed using a PC to form the RF image.

In FIG. 4(*a*), since two optical delay lines are required for each tap point, the equivalent area for each unit element of delay is 1100 $\mu m^2$ in the disclosed example architecture, which can be, e.g., over 100 times smaller than the reported all-electrical delay element for the same amount of delay (see, e.g., T. Chu and H. Hashemi).

A key concept in implementation of the disclosed UWB imager embodiments is that an electrical pulse can be optically delayed. That is, if an optical carrier is modulated with an electrical pulse, optically delayed, and demodulated, the recovered electrical pulse is delayed by the amount of the optical delay. The optical delay lines can be implemented using silicon nanophotonic waveguides.

Figure 5A:
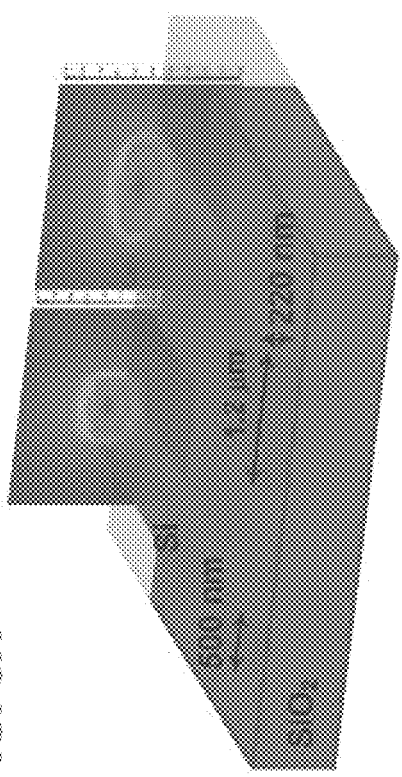
FIG. 5(a) depicts single-mode and multi-mode silicon waveguides on a silicon dioxide layer.
Figure 5C:
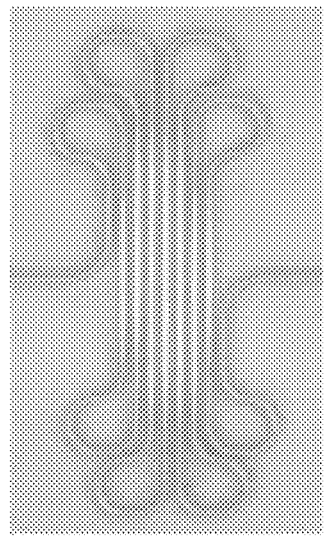
FIG. 5(c) depicts a microphotograph of an implemented TTD sheet.
Figure 5B:
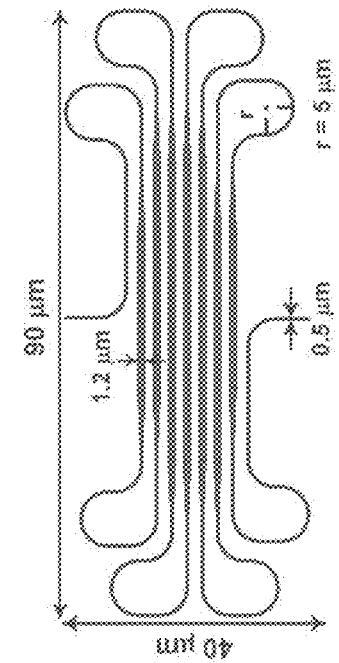
FIG. 5(b) depicts a TTD cell architecture and corresponding dimensions.

FIG. 5(a) shows the structure and the mode profile of the single mode and multimode nanophotonic waveguides used for implementation of the delay line, including the corresponding mode profile when excited by a single-mode source, e.g., at 1550 nm. FIG. 5(b) depicts a TTD cell and corresponding dimensions. Each delay cell in FIG. 5(b), with a delay of 9.8 ps (corresponding to the total length of 800 μm), can be implemented as a meandered waveguide structure where 1.2 mm wide multimode waveguides are used for the straight sections (due to the low propagation loss of 0.3 dB/cm) and 500 nm wide single mode waveguides are used to create the smaller bend structure enabling realization of more compact delay cells. The transition between multimode and single mode waveguides is implemented using tapered waveguides (see FIG. 6). FIG. 5(c) illustrates a microphotograph of the implemented YID element depicted in FIG. 5(b).

FIG. 6 shows the top-level block diagram of an implemented MB imager, in accordance to embodiments described herein. In an embodiment, a laser emitting 30 mW at 1550 nm can be coupled into the chip input nanowaveguide using grating couplers. The coupled light is then split into four branches using Y-junctions and guided to four p-n ring modulators using waveguides with different lengths. The impinging UWB signals are received by a 2×2 array UWB antennas, A1 to A4 with 7 cm spacing, amplified using low-noise amplifiers (LNA) followed by driving amplifiers, and used to modulate the input optical wave to each ring modulator, up-converting the UWB signals to optical domain. The light at the output of each ring modulators is guided to a 1D array of tapped delay-line network composed of TTD delay cells and unequal directional couplers such that the same amount optical power is delivered to each column. Using a similar 1D array in the columns, all four modulated optical signals are combined and connected to the photodiodes that can be considered as the pixels of the imager.

Because a single coherent laser is used in this system, at the points of combination, depending on the instantaneous phase of each the four optical signals, they can interfere constructively, destructively, or any other conditions in between. resulting in variation of signal intensity at the pixels. To address this issue, first the frequency of the input laser can be chirped. Then, the light is coupled to the chip and is split into four signals.

Before reaching the ring modulators, each of the four optical signals goes through a different amount of on-chip delay. Therefore, because the frequency of the laser changes with time (frequency chirping), the frequency of the light going through each ring modulator is different from others. This results in different optical frequencies when the signals are combined at the pixels which solves the problem of phase coherence.

Once the four signals are combined and photodetected, the image can be formed. However, the modulators are being driven with large input UWB signals and due to electromagnetic coupling, these signals appear at the outputs. To solve this issue of cross-talk, the photodiode outputs can be measured using differential energy detection circuitry, i.e., the difference between two adjacent photodiodes is measured. The chip can be fabricated in, e.g., IME 180 nm silicon-on-insulator (SOI) process, and an exemplary chip microphotograph is shown in FIG. 6.

Figure 7A:
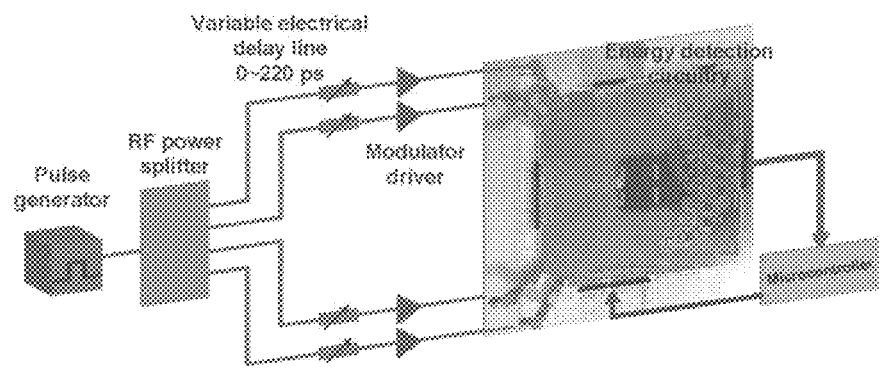
FIGS. 7(a)-(d) depict wired and wireless measurement setups for chip characterization.

To characterize the imager chip, first four variable delay lines are used to simulate receiving the UWB signal from different directions (wired measurement). FIG. 7(a) shows the wired measurement setup. Here, the monocycle pulse generator is connected to four variable delays. Each variable delay can be accurately adjusted over the range of 0 to 220 ps with a resolution of 0.06 ps. The delayed signals are amplified and applied to the ring modulators. By appropriately setting the delays, it is possible to move the highest intensity pixel across the 11×11 matrix. A microcontroller is used to select each of the 11 columns of the imager and to read the outputs of the photodiodes of the same column.

Figure 7B:
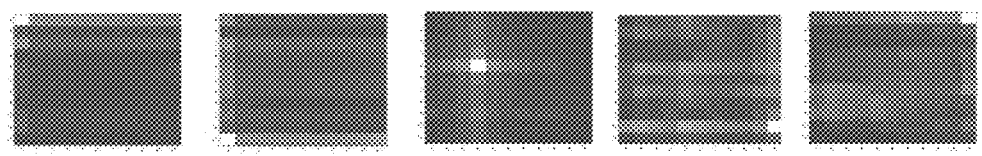

The resulting images for five different settings are shown in FIG. 7(b). It should be noted that chirping the frequency of the input laser can make measurement results more repeatable by addressing phase coherence.

Figure 7C:
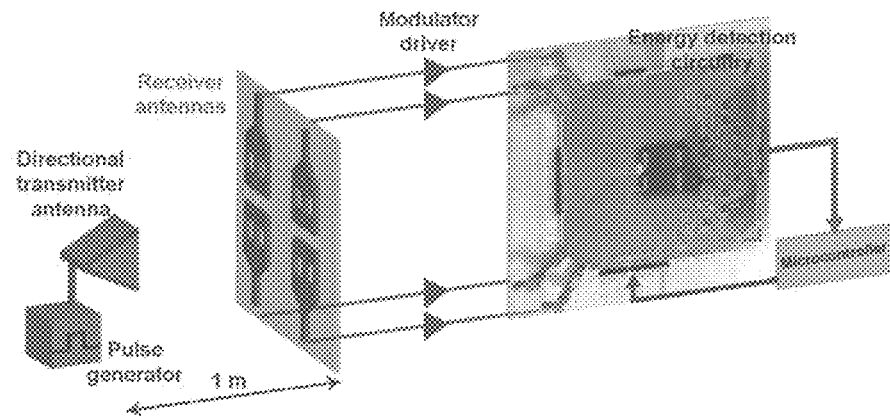
Figure 7D:
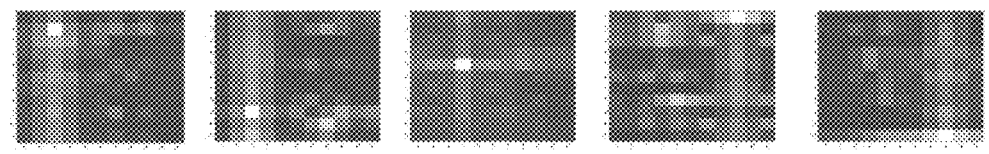

The same experiment can be done sending the UWB using a transmitter antenna to the 2×2 receiver antenna array, which essentially eliminates variable delay lines. FIG. 7(c) shows the wireless measurement setup. Here, the transmitter is placed at a distance of 1 m from the receiver antennas. Equivalent to adjusting the variable delay lines, here the transmitter is moved with respect to the receiver in order to shift the highest intensity pixel across the image. The results of this non-limiting experiment are shown in FIG. 7(d). It should be noted that to minimize the effect of signal reflections and unwanted electromagnetic interference the experiment is done inside an anechoic chamber.

Figure 8A:
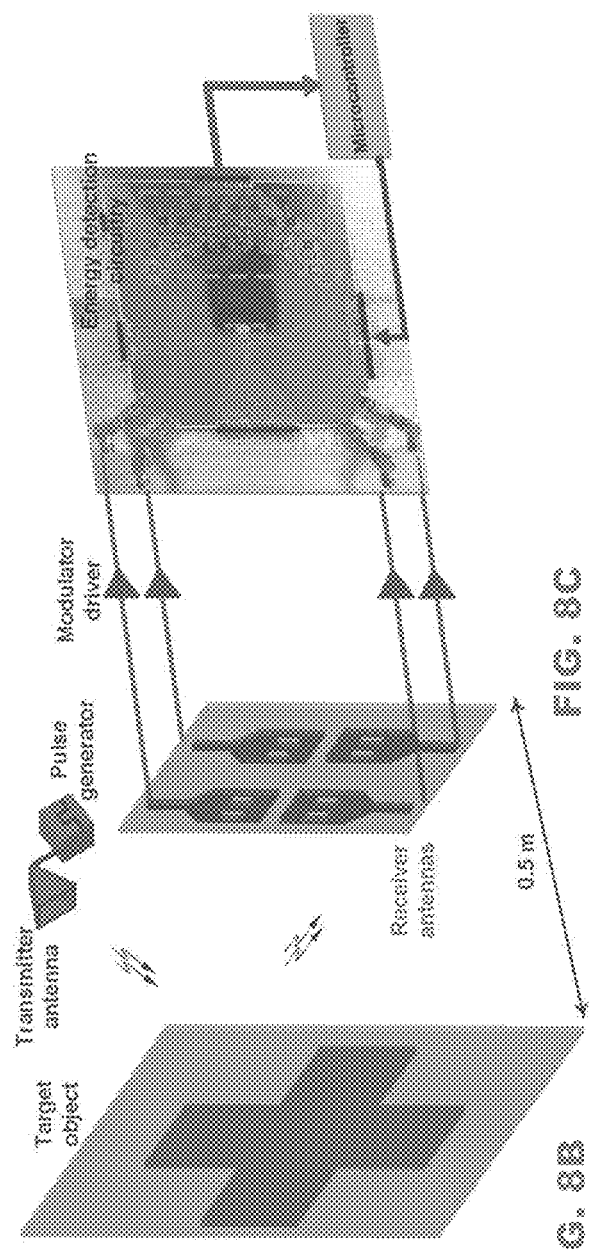
FIGS. 8(a)-(c) depict imaging aspects of a UWB imager chip.
Figure 8C:
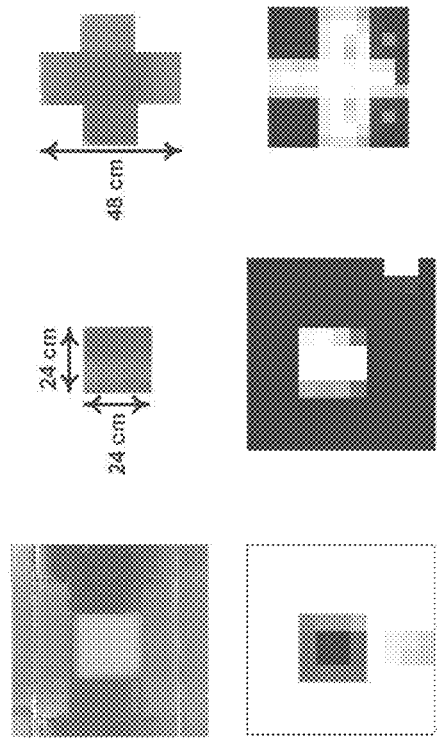
Figure 8B:
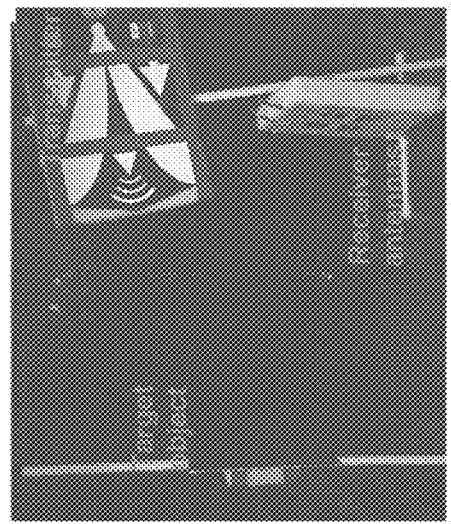

Finally, the chip is used to perform imaging of metallic objects. As shown in FIG. 8(a), the transmitter antenna sends the pulse generator output towards the object placed about 0.5 m away from the receiver antenna array. The received signals are amplified and connected to the chip as explained before. FIG. 8(b) shows the transmitter, target object, and receiving antennas inside the anechoic chamber. A. metallic surface with a 24 cm×24 cm square hole at the center, a metallic square (with the same size as the hole), and a metallic cross are chosen for imaging demonstration. The dimensions of the objects are chosen based on the spatial angle range that the photonic chip covers as well as the distance between the object and the receiver. FIG. 8(c) shows the imaging results for the three objects where the shape of each object can be clearly observed.

Conventionally electrical TTD based UWB antenna arrays are implemented using transmission lines or LC segments that suffer from large TTD element size and power loss as well as sensitivity to electromagnetic interference. The disclosed nanophotonic UWB imager embodiments benefit from photonic nanowavguides to implement the TTD elements with an order of magnitude small size, significantly lower power consumption and insensitive to RF interference.

As mentioned before, a single coherent laser source is used as the optical carrier signal that is modulated by the incoming UWB signals and to solve the phase coherence issue, the frequency of the laser is chirped and by having different on-chip delays it is possible to perform repeatable imaging. Another alternative to this solution is to use incoherent (large linewidth) laser source to ensure that there would be no variations in the optical power when four optical signals are combined at the pixels. In this case, the ring modulator can be wideband enough such that with a large linewidth optical input it can provide enough modulation depth.

One important consideration for antenna arrays and imagers is their large scale implementation. Scaling can happen in number of antennas as well as number of pixels of the imager. Increasing the number of antennas results in higher signal to noise ratio at the pixels. In this case, instead of having antennas at the corners of a square, they can be placed in a circular way and the TTD elements can be inside the circle. In order to scale up the number pixels of the imager, similar 1D array of tapped delay-line network can be used with more number of delay cells and unequal directional couplers. Uneven coupling ratios (e.g. less than 1% to 99%) can be used. One solution is using multiple smaller imagers to form a larger one. For instance, four 11×11 imagers can be put in shape of a larger square to form a 22×22 imager Exemplary Embodiments The following embodiments are illustrative only and do not necessarily limit the scope of the present disclosure of the appended claims.

Embodiment 1. A system comprising: a first modulator configured to convert a radio-frequency signal to an optical signal; a first optical delay line configured to delay, by a first amount, a first optical signal based on the optical signal output by the first modulator; a second optical delay line configured to delay, by a second amount, a second optical signal based on the optical signal output by the first modulator; and at least one photodetector configured to convert optical signals from the first and second delay lines to at least one electrical signal, wherein the at least one electrical signal corresponds to at least one pixel of a radio frequency image.

Embodiment 2. The system of Embodiment 1, further comprising: an imaging module configured to determine a value for the least one pixel of the radio-frequency image based at least in part on the at least one electrical signal.

Embodiment 3. The system of any one of Embodiments 1-2, further comprising a first antenna configured to receive the radio-frequency signal, the first antenna electrically connected to the first modulator.

Embodiment 4. The system of Embodiment 3, further comprising a second antenna configured to receive the radio-frequency signal, the second antenna electrically connected to a second modulator.

Embodiment 5. The system of any one of Embodiments 1-4, wherein the first optical delay line comprises at least one of a nano-waveguide propagation delay, a resonator group delay, or an optical resonator.

Embodiment 6. The system of any one of Embodiments 1-5, wherein the first modulator comprises a ring modulator.

Embodiment 7. The system of any one of Embodiments 1-6, wherein at least one of the first and second optical delay lines comprises a meandered waveguide.

Embodiment 8. The system of any one of Embodiments 1-7, further comprising: at least one processor; and at least one memory comprising processor-executable instructions that, upon execution by the at least one processor, cause the system at least to: form a radio-frequency image based at least in part on output of the photodetector.

Embodiment 9. The system of any one of Embodiments 1-8, wherein processing for the radio-frequency image is performed in the optical domain.

Embodiment 10. A system, comprising: an antenna; a modulator that receives an electrical signal from the antenna; an array of optical delays that receives an optical signal from the modulator; and a photodetector that receives an optical signal from the array of optical delays.

Embodiment 11. The system of Embodiment 10, wherein output of the photodetector corresponds to a pixel of a target image.

Embodiment 12. The system of any one of Embodiments 10-11, wherein a value for the pixel is determined by optical-domain processing.

Embodiment 13. The system of any one of Embodiments 10-12, further comprising: at least one processor; at least one memory comprising processor-executable instructions that, upon execution by the at least one processor, cause the system at least to: form a radio-frequency image based at least in part on output of the photodetector.

Embodiment 14. The system of any one of Embodiments 10-13, wherein the optical delays occupy less surface area than an electrical delay line providing an equivalent amount of delay.

Embodiment 15. A method, comprising: generating, based on a radio-frequency signal received by a first antenna, a first optical signal; generating, based on a radio-frequency signal received by a second antenna, a second optical signal; generating a plurality of delayed optical signals by supplying the first and second optical signals to an array of optical delays; and generating an output signal corresponding to a pixel of a target image, based at least in part on the plurality of delayed optical signals.

Embodiment 16. The method of Embodiment 15, further comprising: forming a radio-frequency image based at least in part on the pixel.

Embodiment 17. The method of any one of Embodiments 15-16, further comprising: providing the first and second antennas and the array of optical delays on an integrated circuit.

Embodiment 18. The method of Embodiment 17, wherein the optical delays occupy less surface area than an electrical delay line providing an equivalent amount of delay.

Embodiment 19. The method of any one of Embodiments 15-18, wherein the first optical signal is supplied to the array of optical delays based at least in part on output of a ring modulator.

Embodiment 20. The method of any one of Embodiments 15-19, wherein the output signal corresponding to the pixel is generated based at least in part by a photodetector.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term: "or" is used in its inclusive sense (and not in its exclusive sense) so that when used, for example, to connect a list of elements, the term "or" means one, some, or all of the elements in the list.

While various aspects and embodiments have been disclosed herein, other aspects and embodiments will be apparent to those skilled in the art. The various aspects and embodiments disclosed herein are for purposes of illustration and are not intended to be limiting.

REFERENCES

E. M. Staderini, "UWB radars in medicine," IEEE Aerospace and Electronic Systems Magazine, vol. 17, Issue 1, Page: 13-18, 2002.

LifeWave Biomedical [on-line], at http://www.lifewavebiomed.com.

E. McEwan, "Body monitoring and imaging apparatus and method," U.S. Pat. No. 5,573,012, 1996.

Xu Yong, Lu Yinghua, Zhang Hongxin, Wang Yeqiu, "An Overview of Ultra-Wideband Technique Application for Medial Engineering," IEEE/ICME International Conference on Complex Medical Engineering(CME), Beijing, May 2007.

K. W. Tan; C. M. Lai; P. H. Lu; C. H. Tu; J. M. Wu, S. H. Hsu, G. W. Huang, and T. Chu, "A 79 GHz UWB pulse-compression vehicular radar in 90 nm CMOS," in Microwave Symposium Digest (MTT). vol. 1, no. 3, pp. 17-22, June 2012.

A. Novack, Y. Liu, R. Ding, M. Gould, T. Baehr-Jones, Q. Li, Y. Yang, Y. Ma, Y. Zhang, K. Padmaraju, K. Bergmen, A. E. J. Lim, G. Q. Lo, and M. Hochberg, "A 30 GHz silicon photonic platform," in Proc. SPIE 8781, Integrated Optics: Physics and Simulations, 2013.

Y. Ma, Y. Zhang, S. Yang, A. Novack, R. Ding, A. E. Lim, G. Q. Lo GQ, T. Baehr-Jones, and M. Hochberg, "Ultralow loss single layer submicron 5 silicon waveguide crossing for SOI optical interconnect," Optics Express, vol. 24, no. 21, 2013.

Liuqing Yang and G. B. Giannakis, "Ultra-wideband communications: an idea whose time has come," in IEEE Signal Processing Magazine, vol. 21, no. 6, pp. 26-54, November 2004.

H. Hashemi, T. s. Chu and J. Roderick, "Integrated true-time-delay-based ultra-wideband array processing," in IEEE Communications Magazine, vol. 46, no. 9, pp. 162-172, September 2008.

T. Chu, J. Roderick and H. Hashemi, "An Integrated Ultra-Wideband Timed Array Receiver in 0.13 ▢m CMOS Using a Path-Sharing True Time Delay Architecture," in IEEE Journal of Solid-State Circuits, vol. 42, no. 12, pp. 2834-2850, December 2007.

T. S. Chu and H. Hashemi, "True-Time-Delay-Based Multi-Beam Arrays," in IEEE Transactions on Microwave Theory and Techniques, vol. 61, no. 8, pp. 3072-3082, August 2013.

S. Kidera, T. Sakamoto and T. Sato, "High-Resolution 3-D imaging Algorithm With an Envelope of Modified Spheres for UWB Through-the-Wall Radars," in IEEE Transactions on Antennas and Propagation, vol. 57, no. 11, pp. 3520-3529, November 2009.

X. Liang, J. Deng, H. Zhang, and T. A. Gulliver "Ultra-Wideband Impulse Radar Through-Wall Detection of Vital Signs", Scientific Reports 8, Article number: 13367, 2018

M. R. Mahfouz, C. Zhang, B. C. Merkl, M. J. Kuhn and A. E. Fathy, "Investigation of High-Accuracy Indoor 3-D Positioning Using UWB Technology," in IEEE Transactions on Microwave Theory and Techniques, vol. 56, no. 6, pp. 1316-1330, June 2008.

C. T. Rodenbeck et al., "Ultra-wideband low-cost phased-array radars," in IEEE Transactions on Microwave Theory and Techniques, vol. 53, no. 12, pp. 3697-3703, December 2005.

P. A. Catherwood and J. McLaughlin, "Internet of Things-Enabled Hospital Wards: Ultrawideband Doctor-Patient Radio Channels," in IEEE Antennas and Propagation Magazine, vol. 60, no. 3, pp. 10-18, June 2018.

H. Song, S. Sasada, T. Kadoya, M. Okada, K. Arihiro, X, Xiao, and T. Kikkawa, "Detectability of Breast Tumor by a Hand-held Impulse-Radar Detector: Performance Evaluation and Pilot Clinical Study", Scientific Reports 7, Article number: 16353, 2017

A. Rahman, M. T. Islam, M. J. Singh, S. IKibria, and Md. Akhtaruzzaman, "Electromagnetic Performances Analysis of an Ultra-wideband and Flexible Material Antenna in Microwave Breast Imaging: To Implement A Wearable Medical Bra", Scientific Reports 6, Article number: 38906, 2016

Y. Lee, et al, "A Novel Non-Contact Heart Rate Monitor Using Impulse-Radio Ultra-Wideband (IR-UWB) Radar Technology", Scientific Reports 8, Article number: 13053, 2018

S. Brovoll, T. Berger, Y. Paichard, Ø. Aardal, T. S. Lande and S. Hamran, "Time-Lapse Imaging of Human Heart Motion With Switched Array UWB Radar," in IEEE Transactions on Biomedical Circuits and Systems, vol. 8, no. 5, pp. 704-715, October 2014.

R. Chavez-Santiago and I. Balasingham, "Ultrawideband Signals in Medicine [Life Sciences]," in IEEE Signal. Processing Magazine, vol. 31, no. 6, pp. 130-136, November 2014.

I. Immoreev and I. H. Tao, "UWB radar for patient monitoring," in IEEE Aerospace and Electronic Systems Magazine, vol. 23, no. 11, pp. 11-18, November 2008.

F. Elbahhar, A. Rivenq, M. Heddebaut and J. M. Rouvaen, "Using UWB Gaussian pulses for inter-vehicle communications," in IEE Proceedings-Communications, vol. 152, no. 2, pp. 229-234, 8 Apr. 2005.

T. Kikkawa, P. K. Saha, N. Sasaki and K. Kimoto, "Gaussian Monocycle Pulse Transmitter Using 0.18 ▢m CMOS Technology With On-Chip Integrated Antennas for Inter-Chip UWB Communication," in IEEE Journal of Solid-State Circuits, vol. 43, no. 5, pp. 1303-1312, May 2008.

S. Park and S. Jeon, "A 15-40 GHz CMOS True-Time Delay Circuit for UWB Multi-Antenna Systems," in IEEE Microwave and Wireless Components Letters, vol. 23, no. 3, pp. 149-151, March 2013.

A. S. Nagra and R. A. York, "Distributed analog phase shifters with low insertion loss," in IEEE Transactions on Microwave Theory and Techniques, vol. 47, no. 9, pp. 1705-1711, September 1999.

J. Roderick, H. Krishnaswamy, K. Newton and H. Hashemi, "Silicon-Based Ultra-Wideband Beam-Forming," in IEEE Journal of Solid-State Circuits, vol. 41, no. 8, pp. 1726-1739, August 2006.

Z. Xuan, Y. Ma, Y. Liu, R. Ding, Y. Li, N. Ophir, A. E. Lim, G. Q. Lo, P. Magill, K. Bergman, T. Baehr-Jones, and M. Hochberg, "Silicon microring modulator for 40 Gb/s NRZ-OOK metro networks in O-band," Opt. Express 22, 28284-28291 (2014)

What is claimed:
1. A system comprising:
   an integrated circuit, comprising:
      a first modulator configured to convert a radio-frequency signal to an optical signal;

a first optical delay line configured to delay, by a first amount, a first optical signal based on the optical signal output by the first modulator; and a second optical delay line configured to delay, by a second amount, a second optical signal based on the optical signal output by the first modulator; and at least one photodetector configured to convert optical signals from the first and second delay lines to at least one electrical signal, wherein the at least one electrical signal corresponds to at least one pixel of a radio frequency image.

2. The system of claim 1, further comprising:

an imaging module configured to determine a value for the least one pixel of the radio-frequency image based at least in part on the at least one electrical signal.

3. The system of claim 1, further comprising:

a first antenna configured to receive the radio-frequency signal, the first antenna electrically connected to the first modulator.

4. The system of claim 3, further comprising:

a second antenna configured to receive the radio-frequency signal, the second antenna electrically connected to a second modulator.

5. The system of claim 1, wherein the first optical delay line comprises at least one of a nano-waveguide propagation delay, a resonator group delay, or an optical resonator.

6. The system of claim 1, wherein the first modulator comprises a ring modulator.

7. The system of claim 1, wherein at least one of the first and second optical delay lines comprises a meandered waveguide.

8. The system of claim 1, further comprising:

at least one processor; and at least one memory comprising processor-executable instructions that, upon execution by the at least one processor, cause the system at least to:

form a radio-frequency image based at least in part on output of the photodetector.

9. The system of claim 1, wherein processing for the radio-frequency image is performed in the optical domain.

10. A system, comprising:

an integrated circuit, comprising:

an antenna;

a modulator that receives an electrical signal from the antenna; and an array of optical delays that receives an optical signal from the modulator; and a photodetector that receives an optical signal from the array of optical delays.

11. The system of claim 10, wherein output of the photodetector corresponds to a pixel of a target image.

12. The system of claim 11, wherein a value for the pixel is determined by optical-domain processing.

13. The system of claim 10, further comprising:

at least one processor;

at least one memory comprising processor-executable instructions that, upon execution by the at least one processor, cause the system at least to:

form a radio-frequency image based at least in part on output of the photodetector.

14. The system of claim 10, wherein the optical delays occupy less surface area than an electrical delay line providing an equivalent amount of delay.

15. A method, comprising:

providing first and second antennas and an array of optical delays on an integrated circuit;

generating, based on a radio-frequency signal received by the first antenna, a first optical signal;

generating, based on a radio-frequency signal received by the second antenna, a second optical signal;

generating a plurality of delayed optical signals by supplying the first and second optical signals to the array of optical delays; and generating an output signal corresponding to a pixel of a target image, based at least in part on the plurality of delayed optical signals.

16. The method of claim 15, further comprising:

forming a radio-frequency image based at least in part on the pixel.

17. The method of claim 15, wherein the optical delays occupy less surface area than an electrical delay line providing an equivalent amount of delay.

18. The method of claim 15, wherein the first optical signal is supplied to the array of optical delays based at least in part on output of a ring modulator.

19. The method of claim 15, wherein the output signal corresponding to the pixel is generated based at least in part by a photodetector.

* * * * *

UNITED STATES PATENT AND TRADEMARK OFFICE
CERTIFICATE OF CORRECTION

| | | |
|---|---|---|
| PATENT NO. | : 11,567,189 B2 | |
| APPLICATION NO. | : 16/969998 | |
| DATED | : January 31, 2023 | |
| INVENTOR(S) | : Firooz Aflatouni et al. | |

It is certified that error appears in the above-identified patent and that said Letters Patent is hereby corrected as shown below:

On the Title Page

In Item (51), In Int. Cl.,

Under Column No. 1, Page 2, Line no. 3, Replace:
"*H01Q 21/00*   (2006.01)
*G01S 13/02*    (2006.01)"
With:
--*G01S 13/02*   (2006.01)--

In Item (56), In Other Publications,

Under Column No. 2, Page 2, Line no. 3, Replace:
"Article No."
With:
--Article No.:--

Under Column No. 2, Page 2, Line no. 5, Replace:
"Article No."
With:
--Article No.:--

Under Column No. 2, Page 2, Line no. 25, Replace:
"a Wearable"
With:
--A Wearable--

Under Column No. 2, Page 2, Line no. 26, Replace:
"Article No."

Signed and Sealed this
Eleventh Day of June, 2024

Katherine Kelly Vidal
*Director of the United States Patent and Trademark Office*

With:
--Article No.:--

Under Column No. 2, Page 2, Line no. 41, Replace:
"40 GB/s"
With:
--40 Gb/s--

In the Specification

Under Column No. 1, Line no. 12, Replace:
"in their"
With:
--in its--

Under Column No. 1, Line no. 32, Replace:
"monitoring; and"
With:
--monitoring, and--

Under Column No. 2, Line no. 29, Replace:
"an imagine"
With:
--an imaging--

Under Column No. 2, Line no. 50, Replace:
"FIG. 1(a)"
With:
--FIG. 1A--

Under Column No. 2, Line no. 52, Replace:
"FIG. 1(b)"
With:
--FIG. 1B--

Under Column No. 2, Line no. 54, Replace:
"FIG. 2(a)"
With:
--FIG. 2A--

Under Column No. 2, Line no. 56, Replace:
"FIG. 2(b)"
With:
--FIG. 2B--

Under Column No. 2, Line no. 59, Replace:
"FIG. 4(a)"
With:
--FIG. 4A--

Under Column No. 2, Line no. 61, Replace:
"FIG. 4(b)"
With:
--FIG. 4B--

Under Column No. 2, Line no. 62, Replace:
"FIG. 5(a)"
With:
--FIG. 5A--

Under Column No. 2, Line no. 64, Replace:
"FIG. 5(b)"
With:
--FIG. 5B--

Under Column No. 2, Line no. 66, Replace:
"FIG. 5(c)"
With:
--FIG. 5C--

Under Column No. 3, Line no. 1, Replace:
"FIG. 6 depicts"
With:
--FIGs. 6A-6B depict--

Under Column No. 3, Line no. 3, Replace:
"FIGS. 7(a)-(d)"
With:
--FIGs. 7A-7D--

Under Column No. 3, Line no. 5, Replace:
"FIGS. 8(a)-(c)"
With:
--FIGs. 8A-8C--

Under Column No. 4, Line no. 48, Replace:
"FIG. 1(b)"
With:
--FIG. 1B--

Under Column No. 4, Line no. 67, Replace:
"will. be"
With:
--will be--

Under Column No. 5, Line no. 2, Replace:
"FIG. 1(b)"
With:
--FIG. 1B--

Under Column No. 5, Line no. 3, Replace:
"FIG. 2(a)."
With:
--FIG. 2A.--

Under Column No. 5, Line no. 4, Replace:
"FIG. 2(a)"
With:
--FIG. 2A--

Under Column No. 5, Line no. 42, Replace:
"optically-assisted"
With:
--optically assisted--

Under Column No. 6, Line no. 1, Replace:
"FIG. 2(a)),"
With:
--FIG. 2A),--

Under Column No. 6, Line no. 4, Replace:
"FIG. 2(b)"
With:
--FIG. 2B--

Under Column No. 6, Line no. 45, Replace:
"FIG. 4(b)."
With:
--FIG. 4B.--

Under Column No. 6, Line no. 58, Replace:
"FIG. 4(a))."
With:
--FIG. 4A).--

Under Column No. 6, Line no. 64, Replace:
"FIG. 4(a),"
With:
--FIG. 4A,--

Under Column No. 7, Line no. 10, Replace:
"FIG. 5(a)"
With:
--FIG. 5A--

Under Column No. 7, Line no. 14, Replace:
"FIG. 5(b)"
With:
--FIG. 5B--

Under Column No. 7, Line no. 15, Replace:
"FIG. 5(b),"
With:
--FIG. 5B,--

Under Column No. 7, Line no. 24, Replace:
"(see FIG. 6). FIG. 5(c)"
With:
--(see FIGs. 6A and 6B). FIG. 5C--

Under Column No. 7, Line no. 26, Replace:
"FIG. 5(b)."
With:
--FIG. 5B.--

Under Column No. 7, Line no. 27, Replace:
"FIG. 6"
With:
--FIG. 6A--

Under Column No. 7, Line no. 28, Replace:
"implemented MB"
With:
--implemented UWB--

Under Column No. 7, Line no. 51, Replace:
"in between."
With:
--in between--

Under Column No. 8, Line no. 5, Replace:
"FIG. 6."
With:
--FIG. 6B.--

Under Column No. 8, Line no. 8, Replace:
"FIG. 7(a)"
With:
--FIG. 7A--

Under Column No. 8, Line no. 20, Replace:
"FIG. 7(b)."
With:
--FIG. 7B.--

Under Column No. 8, Line no. 25, Replace:
"FIG. 7(c)"
With:
--FIG. 7C--

Under Column No. 8, Line no. 31, Replace:
"FIG. 7(d)."
With:
--FIG. 7D.--

Under Column No. 8, Line no. 36, Replace:
"FIG. 8(a),"
With:
--FIG. 8A,--

Under Column No. 8, Line no. 40, Replace:
"FIG. 8(b)"
With:
--FIG. 8B--

Under Column No. 8, Line no. 41, Replace:
"chamber. A."
With:
--chamber. A--

Under Column No. 8, Line no. 47, Replace:
"FIG. 8(c)"
With:
--FIG. 8C--

CERTIFICATE OF CORRECTION (continued)
U.S. Pat. No. 11,567,189 B2

Under Column No. 8, Line no. 55, Replace:
"nanowavguides to"
With:
--nanowaveguides to--

Under Column No. 10, Line no. 64, Replace:
"the term:"
With:
--the term--

Under Column No. 11, Line no. 25, Replace:
"(MTT)."
With:
--(MTT),--

Under Column No. 11, Line no. 28, Replace:
"Bergrnen, A."
With:
--Bergmen, A.--

Under Column No. 11, Line no. 56, Replace:
"3-D imaging"
With:
--3-D Imaging--

Under Column No. 12, Line no. 14, Replace:
"IKibria, and"
With:
--Kibria, and--

Under Column No. 12, Line no. 30, Replace:
"IEEE Signal."
With:
--IEEE Signal--

Under Column No. 12, Line no. 33, Replace:
"I. H."
With:
--T. H.--